United States Patent [19]

Malpass et al.

[11] Patent Number: 4,876,318

[45] Date of Patent: Oct. 24, 1989

[54] ORGANOALUMINUM COUPLING AGENTS AND FILLED POLYMER COMPOSITIONS THEREOF

[75] Inventors: Dennis B. Malpass, LaPorte, Tex.; Kelly B. Triplett, Stamford, Conn.; Andrzej M. Piotrowski, Thornwood, N.Y.

[73] Assignee: Texas Alkyls, Inc., Deer Park, Tex.

[21] Appl. No.: 221,390

[22] Filed: Jul. 19, 1988

[51] Int. Cl.$^4$ ............... C08K 5/56; C07F 7/10; C07F 5/06

[52] U.S. Cl. ................... 525/446; 525/464; 523/213; 524/605; 524/611

[58] Field of Search ............ 524/605, 611, 174; 525/446, 464; 556/173; 523/213

[56] References Cited

U.S. PATENT DOCUMENTS

| | | | |
|---|---|---|---|
| 3,631,192 | 12/1971 | Michael | 556/173 |
| 3,905,936 | 9/1975 | Geoffrey | 523/202 |
| 4,357,271 | 11/1982 | Rosenquist | 524/611 |

FOREIGN PATENT DOCUMENTS

| | | | |
|---|---|---|---|
| 53-106750 | 9/1978 | Japan | 524/605 |
| 55-084351 | 6/1980 | Japan | 524/605 |

OTHER PUBLICATIONS

Kawaken; Abstract of Japan 62-225,540; 10/87.
Belo; Abstract of USSR, 1,150,252; 4/85.
Kawaken; Abstract of Japan 57-205,431; 12/82.
Kawaken; Abstract of Japan 60-079,068; 5/85.
Ajinomoto; Abstract of Japan 60-217,270; 10/85.

*Primary Examiner*—Lewis T. Jacobs
*Attorney, Agent, or Firm*—Richard P. Fennelly; Louis A. Morris

[57] ABSTRACT

Compounds of the formula

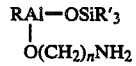

where R is alkyl, R' is independently selected from alkyl and aryl, and n ranges from 1 to 8 are useful as coupling agents in filled polymer compositions, e.g., in filled, polar polymers such as polybutylene terephthalate.

8 Claims, No Drawings

ORGANOALUMINUM COUPLING AGENTS AND FILLED POLYMER COMPOSITIONS THEREOF

BACKGROUND OF THE INVENTION

1. Field of the Invention

The present invention relates to organoaluminum compounds which find utility as coupling agents in filled polymer systems.

2. Description of the Prior Art

Coupling agents are compounds that promote adhesion between organic polymers and fillers. Such improved adhesion can lead to better overall mechanical properties of the final composite material. Currently available coupling agents include derivatives of silicon, titanium, zirconium and chromium.

There exist certain disclosures in the prior art in regard to the use of organoaluminum compounds to coat particulate materials in polymer substrates. U.S. Pat. No. 3,905,936 describes use of compounds of the formula $(RO)_n AlR'_{3-n}$, where R is an aliphatic or aromatic hydrocarbyl group, R' is a carboxylate or oxy radical and n is 1 or 2. European Patent Application No. 198,374 describes certain aluminum compounds containing an aluminumalkoxy or aluminum aryloxy bond. The other two substituents bonded to the aluminum central atom can be alkoxy, aryloxy, acyloxy, alkylphosphate, alkylsulfate, monohydroxy ester, monoacyloxy ester and their substituted derivatives.

SUMMARY OF THE PRESENT INVENTION

One aspect of the present invention relates to compounds of the formula

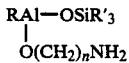

where R is alkyl, R' are any one of alkyl or aryl, and n ranges from 1 to 8. Another aspect of the present invention relates to filled polymer compositions containing these compounds as coupling agents.

DETAILED DESCRIPTION OF THE PRESENT INVENTION

The compounds depicted above, which function as coupling agents in filled polymer formulations, are believed to be novel and can easily be formed by the reaction of a compound of the formula

where R and R' are as previously defined, with a compound of the formula

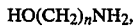

where n is as defined above. The reaction can be conducted with the neat materials, in the absence of solvent, if desired.

The resulting coupling agent of the instant invention is of the formula depicted under the heading "Summary of the Present Invention". It is highly preferred that the substituents R' in the above formula not all be selected from relatively bulky groups such as phenyl, alkyl substituted phenyl (e.g., t-butyl phenyl), or branched alkyl (e.g., t-butyl, isopropyl, and the like) since three such bulky groups on the silicon atom of the molecule can give rise to an undesired degree of steric hindrance. Such steric hindrance can result in a compound exhibiting substantially less activity as an effective coupling agent in filled polymer systems than an analogous compound of similar structure having less bulky R' groups. For example, a compound having three phenyl groups only showed some acceptable activity, in accordance with a predictive screening test, compared to the compound of Example 1 as well as a control, in polybutylene terephthalate resins.

The polymeric substrates which can be chosen for use with the above coupling agents include such resins as polyester resin (e.g., polybutylene terephthalate) as well as nylon and polycarbonate resins. A variety of mineral fillers can be used in filled polymer compositions containing the coupling agent compounds of this invention including: talc; glass fiber; fumed silica; and the like. Representative amounts of filler in the polymeric substrate range from about 5% to about 50%. The coupling agent can be present at from about 0.05% to about 10%, by weight of the filler.

The foregoing invention is illustrated by the Examples which follow.

EXPERIMENTAL

A. General Procedures

All preparation and reactions involving air- and moisture-sensitive organoaluminum compounds were conducted under an atmosphere of dry, oxygen-free nitrogen. All starting alcohols were used as received without any further purification. Proton magnetic resonance spectra ($^1$H-NMR) were obtained with a Varian spectrometer, Model EM-360, on 10% solutions in CDCl$_3$ or deuterated DMSO.

B. Screening Test for Coupling Agent Candidates

This screening test was used as a predictor for utility of the coupling agent compounds of the instant invention in filled polymer systems.

A testing procedure using a microscope slide as a model of the inorganic surface has been developed. Microscope slides (Fisher Scientific premium grade, 3"×1"×1.2 mm) were used without any additional cleaning. The slides were submerged in toluene in an open beaker or Soxhlet extractor when a nitrogen blanket was used. A stand (TEFLON brand polymer) was used to prevent the slides from sticking to each other. Coupling agent was added in a 10% or 20% solution up to 100° C. temperature for ten minutes (in a well-ventilated bay). The slides were then removed, washed with clean solvent (or washed under a nitrogen blanket by distilling solvent in the Soxhlet apparatus), and were dried at 105° C. for at least ten minutes. Slides to be tested were placed on a hot plate set between 195° C. and 207° C. (with temperature variation of about ±2.5° C.), depending on the polymer type used, and thermoplastic polymers were melted on the glass surface. Melted polymer was spread by applying pressure through TEFLON brand foil. When desired, a small square piece of thermoplastic resin was melted at the edge and was attached to the polymer spread on the glass. This piece was used to attached weight during adhesion tests. After cooling, adhesion was tested by visual observation and applying load to achieve disconnection. Before force was applied, the plastic surface was trimmed to about 3 cm$^2$. Specimens were tested by first placing an 11 kilogram weight on an electronic balance which was then rezeroed. The plastic test specimen on the glass slide was attached to the weight by a support where the glass slide was supported on both sides of its point of attachment to the specimen and was moved upwardly away from the weight and electronic balance. A reading was taken at the point of failure. When good coupling agents were used with rigid polymers (PC, nylon, PBT) with very different than glass linear thermal expansion coefficient, polymer was often peeled with the film of glass still attached to it with little or no force (due to stress).

An empirical scale of adhesion strength was devised:

0—NO ADHESION (polymer falls off with little or no applied force)

1—LOW ADHESION (polymer peels easily with load less than 0.5 kg)

2—MODERATE ADHESION (polymer peels off with load less than 2 kg but more than 0.5 kg)

3—GOOD ADHESION (polymer peels with load less than 4 kg but more than 2 kg)

4—EXCELLENT ADHESION (polymer does not peel without damage to the glass or resin, usually 9 to 10 kg load).

EXAMPLE 1

The compound

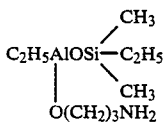

was synthesized by placing $(C_2H_5)_2AlOSi(CH_3)_2(C_2H_5)$, 20 millimoles in 20 milliliters of $CH_2Cl_2$, in a flask equipped with a nitrogen inlet and a reflux condenser. Aminopropanol (20 millimoles) was added by syringe over a period of 20 minutes. Vigorous reflux and extensive gas evolution was observed. After the addition was completed, the reaction mixture was stirred at room temperature for one hour. The solvent was evaporated by warming up to reflux, and the remaining $CH_2Cl_2$ was stripped under vacuum overnight. A total of 4.75 grams of the above-depicted compound was isolated.

EXAMPLE 2

The Table set forth below reports the adhesion results for the compound of Example 1.

| Resin | Control | Example 1 |
|---|---|---|
| ABS | 0 | 0 |
| HDPE[1] | 1 | 0 |
| LLDPE[3] | 4 | 4 |
| Nylon[4] | 0–3 | 4 |
| PBT | 0 | 4 |
| PC[5] | 0 | 4 |
| PMMA[6] | 0 | 0 |
| Impact PS[7] | 0 | 0 |
| PET[8] | 3 | 3 |
| PP | 0 | 0 |
| SAN[9] | 2 | NT[2] |

[1]High density polyethylene.
[2]Not tested.
[3]Linear low density polyethylene.
[4]Most tests showed little or no adhesion. Some tests show ratings of 3, believed due to lack of precise temperature control during treating.
[5]Polycarbonate.
[6]Polymethylmethacrylate.
[7]Polystyrene.
[8]Polyethylene terephthalate.
[9]Styrene-acrylonitrite copolymer.

The compound of Example 1 was quite effective for such polar polymers as polybutylene terephthalate and polycarbonate.

The foregoing Examples are intended to illustrate certain embodiments of the instant invention and should not be construed in a limiting sense. The scope of protection sought is given in the claims which follow.

We claim:

1. Compounds of the formula

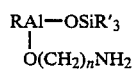

where R is alkyl, R' is independently selected from alkyl and aryl, and n ranges from 1–8.

2. A compound as claimed in claim 1 where R is ethyl, R' is selected from the group consisting of methyl and ethyl, and n is equal to 3.

3. A compound as claimed in claim 1 where R is ethyl, R' are methyl, methyl and ethyl, respectively, and n is equal to 3.

4. A filled polymer comprising a polymer substrate, filler, and a compound as claimed in claim 1 as a coupling agent.

5. A filled polymer comprising a polar polymer substrate, filler, and the compound of claim 2 as the coupling agent.

6. A filled polymer as claimed in claim 5 where the polymer substrate is polybutylene terephthalate.

7. A filled polymer as claimed in claim 5 where the polymer substrate is polycarbonate.

8. A filled polymer comprising a polybutylene terephthalate substrate, filler, and a compound as claimed in claim 3 as the coupling agent.

* * * * *